United States Patent [19]

Mazur et al.

[11] 3,963,765

[45] June 15, 1976

[54] PREPARATION OF DERIVATIVES OF CHOLESTEROL

[76] Inventors: Yehuda Mazur, 14 Haknesset Hagdola St., Tel Aviv; Avner Rotman, 8 Hagoren St., Rehovot, both of Israel

[22] Filed: July 11, 1974

[21] Appl. No.: 487,432

Related U.S. Application Data

[63] Continuation-in-part of Ser. No. 454,394, March 25, 1974, Pat. No. 3,920,531.

[30] Foreign Application Priority Data

Apr. 1, 1973 Israel.................................. 41923

[52] U.S. Cl.............................. 260/397.2; 204/159; 204/162 R
[51] Int. Cl.$^2$............................................. C07J 9/00
[58] Field of Search............................... 260/397.2

[56] References Cited
UNITED STATES PATENTS

| | | | |
|---|---|---|---|
| 3,697,559 | 10/1972 | DeLuca et al. | 260/397.2 |
| 3,786,062 | 1/1974 | Schroeder et al. | 260/397.2 |

*Primary Examiner*—Elbert L. Roberts
*Attorney, Agent, or Firm*—Hubbell, Cohen, Stiefel & Gross

[57] ABSTRACT

Process for the production of hydroxylated derivatives of cholesterol and 7-dehydrocholesterol which comprises subjecting a saturated unsubstituted or substituted derivative of cholestane, dissolved in a suitable solvent, in the presence of peracetic acid, to irradiation with ultra-violet radiation of a wavelength below 350m$\mu$, or heating in a suitable solvent, separating the reaction products, which if desired, are converted to other derivatives, and recovering the residue of the starting material. Novel derivatives are obtained and these are: 3$\beta$-acetoxy,25-hydroxy,5$\alpha$-cholestane; 3$\beta$-acetoxy, 5$\alpha$,25-dihydroxy cholestane; 3$\beta$,5$\alpha$,25-trihydroxy cholestane; 3-keto, 5$\alpha$,25-dihydroxy cholestane; 3-keto,25-hydroxy-$\Delta^4$-cholestane; 3$\beta$,25-diacetoxy-5$\alpha$-hydroxy-cholestane; 3$\beta$-acetoxy, 25-trichloroacetoxy-5$\alpha$-hydroxy-cholestane, 25-trichloroacetoxy-cholesterol and 25-acetoxy-cholesterol.

12 Claims, No Drawings

PREPARATION OF DERIVATIVES OF CHOLESTEROL

CROSS-REFERENCE TO RELATED APPLICATIONS

This application is a continuation-in-part of application Ser. NO. 454,394 filed Mar. 25, 1974, now U.S. Pat. No. 3,920,531.

BACKGROUND OF THE INVENTION:

A number of hydroxylated derivatives of cholocalciferol have been isolated as metabolites of cholecalciferol, and these have been found to be more potent than the parent compound, vitamin $D_3$. Thus, 25-hydroxy- 21,25-dihydroxy- and 1,25-dihydroxy-cholecalciferol exhibit distinctive physiological activity and are of substantial importance in medicine.

According to the present invention there is provided a novel and simple process for the preparation of hydroxylated derivatives of cholesterol and of 7-dehydroxycholesterol, which are intermediates in the preparation of these and of other hydroxylated derivatives of cholecalciferol.

SUMMARY OF THE INVENTION:

The present invention relates to the preparation of hydroxylated derivatives of cholesterol and 7-dehydrocholesterol and to the preparation of cholecalciferol and of derivatives of this latter compound.

The process of the present invention comprises subjecting a saturated unsubstituted or substituted cholestane derivative, dissolved in a suitable solvent, in the presence of peracetic acid, to irradiation with u.v. light having a wavelength below 350 m$\mu$ or to heating in a suitable solvent, which results in the introduction of a hydroxy group in the tertiary position of the cholestane skeleton.

As the main product of the reaction there is obtained the 25-hydroxy derivative of the starting material. Thus 3$\beta$-acetoxy, 5$\alpha$-cholestane (I) and 3$\beta$-acetoxy, 5$\alpha$-hydroxy cholestane (II) resulted in the corresponding 25-hydroxy derivatives, (III) and (IV). In addition to these, further tertiary-hydroxylated derivatives were isolated.

The derivative (IV) was converted by a sequence of reaction steps to the 25-hydroxylated 7-dehydrocholesterol (V). The sequence of reaction steps is illustrated in the following: Compound (IV) was hydrolyzed with methanolic potassium hydroxide to 3$\beta$,5$\alpha$,25-trihydroxy-cholestane (VI), which was oxidized by means of chromic acid to the corresponding 3-keto-derivative (VII). The latter was dehydrated with acid to the corresponding $\Delta^4$-3-keto-derivative (VIII). The conversion of (VIII) of the 25-hydroxy-7-dehydro-cholesterol (V) is effected by conventional means, similar to those described with reference to the preparation of 7-dehydro-cholesterol derivatives by Pelc et al., J. Chem, Soc. (C), 3415 (1971).

Another route from 3$\alpha$-acetoxy 5 ,25-dihydroxy-cholestane (IV) to the 25-hydroxy-7-dehydrocholesterol (V) involves the preparation of the intermediate 25-hydroxy-cholesterol (IX) this may be done by preferential esterification of (IV) with either trichloroacetic anhydride or with acetic anhydride to the respective esters (X) and (XI). These esters are then dehydrated with thionyl chloride/pyridine, and with other suitable dehydrating reagents to give the respective 25-cholesterol esters (XII) and (XIII). Hydrolysis of either of the two latter compounds results in the 25-hydroxycholesterol (IX). 25-hydroxy-cholesterol (IX) was also obtained from $\Delta^4$-3-keto cholestane (VIII) by reduction of its enol acetate (X) with sodium borohydride.

The conversion of IX to V has been previously reported by S.J. Halkes and N.P. Van Vliet Recueil Trav. Chim. 88, 1080 (1969).

DESCRIPTION OF THE PREFERRED EMBODIMENT

Example 1:

A solution of 15 g of 3$\beta$-acetoxy-5 -cholestane (I) in 250 cc of ethyl acetate was treated with 30 cc peracetic acid (40%) in acetic acid and was irradiated with ultra-violet light of at about 300 m$\mu$ wavelength for 24 hours. The resulting reaction mixture was washed consecutively with an aqueous solution of sodium bisulfite, sodium bicarbonate and water and the solvents were evaporated in vacuo to dryness. The residue was chromatographed on a column of silica gel to give 3.5 g of the known 3$\beta$-acetoxy-25-hydroxy-5$\alpha$-cholestane (III), m.p. 125°–126°C and 1.8 g of the known 3$\beta$-acetoxy-5$\alpha$-hydroxy-cholestane (II), m.p. 180°–181°C.

Example 2:

A solution of 50 g 3$\beta$-acetoxy-5-$\alpha$-hydroxy-cholestane (II), in 25 ml. of ethyl acetate was treated with 100 ml. of peracetic acid (70%) in acetic acid and was irradiated with ultra-violet light of about 300 m$\mu$ wavelength for 12 hours. The resulting reaction mixture was washed with a solution of aqueous sodium bisulfite, sodium bicarbonate and then with water. After evaporation of the solvent in vacuo, the residue was chromatographed on a column of silica gel to give 10 g of the novel 3$\beta$-acetoxy-5$\alpha$,25-dihydroxy cholestane (IV) which was recrystallized from methanol, m.p. 180°–182°C.

Nmr$_\delta$ $\delta$ 0.67 (s, 1H), 1.0 (s, 3H), 0.90 (d, J=5Hz, 3H), 1.20 (s, 6H) and 2.02 (s, 3H), Anal. Calcd. for $C_{29}H_{50}O_4$: C, 75.3%; H, 10.9%. Found C, 75.4; H, 10.9%.

Example 3:

A solution of 3$\beta$-acetoxy-5$\alpha$,25-dihydroxy-cholestane (IV) in 40 cc of methanol and 10 cc of dioxane was treated with 6 cc of a 10% solution of sodium hydroxide and refluxed for 3 hours. The reaction mixture was neutralized with a solution of 5% aqueous hydrochloric acid, extracted with ether and washed with water. The ether solution was evaporated in vacuo and the residue was recrystallized from ether to give 850 mg of the 3$\beta$, 5$\alpha$,25-tri-hydroxy-cholestane (VI) m.p. 202°–204°Nmr $\delta$ 0.67 (s, 3H), 0.9 (d, J=5 cps, 3H), 1.22 (s, 6H).

Example 4:

A solution of 750 mg of the 3$\beta$,5$\alpha$-25-trihydroxy-cholestane (VI) in 300 ml of acetone was treated dropwise with 10cc of Jones reagent. The reaction mixture was treated with 10 ml of methanol, left for 15 minutes at room temperature and concentrated in vacuum. The residue was extracted with ether and washed with water. The ether extract was evaporated in vacuo and the residue was crystallized from benzene to give 570 mg of 3-keto-5$\alpha$,25-dihydroxy-cholestane (VII) m.p. 215°–217°. Nmr $\delta$ 0.70 (s, 3H), 1.15 (s, 3H), 0.95 (d, J=5Hz, 1H), 1.22 (s, 3H) Anal. Calcd for $C_{27}H_{46}O_2$: C, 77.5; H, 11.1%. Found: C, 77.0; H, 10.5%.

Example 5:

A solution of 950 mg of 3-keto-5,25-dihydroxy-cholestane (VII) in 200 ml of benzene was refluxed for 2.5 hours in the presence of 50 mg of p-toluene sulfonic acid. The product was extracted with ether, and chromatographed on silica gel to give 600 mg of the known 3-keto-25-hydroxy-$\Delta^4$-cholestane, m.p. 142°–144° (VIII).

Example 6

A solution of 280 mg of 3$\beta$-acetoxy, 5$\alpha$,25-dihydroxy-cholestane (VI) in 5 ml of pyridine was treated with 3.5 ml of trichloroacetic anhydride. After 48 hrs at ambient temperature the reaction mixture was poured into ice and the product was isolated from ether and chromatographed on silica gel, The product was recystallized from methanol to give 180 mg of the 3$\beta$-acetoxy-25-trichloroacetoxy-5$\alpha$-hydroxy cholestane (X) .Nmr $\delta$ (0.66 s, 3H), 1.0 (s, 3H), 1.56 (s, 6H), 0.92 (d, J=5Hz, 3H) 2.05 (s, 3H).

Anal. Calcd for $C_{31}H_{49}O_5Cl_3$: C, 61.2, H, 8.1%, Found: C, 61.4; H, 8.12%.

Example 7

A solution of 50 mg of 3$\beta$-acetoxy--25-trichloro-acetoxy-5$\alpha$-hydroxy-cholestane (X) in 2 ml of pyridine was treated with 2 ml of thionyl chloride at 0°C. After being left at ambient temperature for 16 hrs, the reaction mixture was poured on ice extracted with ether and the product chromatographed on silica gel. The resulting material (XII) was dissolved in a mixture of 10 ml of tetrahydrofuran, 2 ml of methanol and 1 ml of potassium hydroxide solution (10%). After being left at ambient temperature for 48 hrs the solution was concentrated in vacuo and the product isolated from ether. It had m.p. 180°–182°C. and was identical with 25-hydroxy-cholesterol (IX).

Example 8

A solution of 1 g of 3$\beta$-acetoxy-5$\alpha$,25-dihydroxy cholestane (IV) in 10 ml of pyridine and 10 ml of acetic anhydride was heated on a steam bath for 1 hr. Isolation from ether and crystallization from methanol resulted in 0.8 g of 3$\beta$,25-diacetoxy-5$\alpha$-hydroxy-cholestane (XI), m.p. 184°–185°; Nmr$\delta$ 0.66 (s, 3H), 1.0 (s, 3H), 1.4 (s, 6H), 1.99 (s, 3H), 2.01 (s, 3H), Anal. Calcd for $C_{31}H_{52}O_5$, C, 73.8; H, 10.4%. Found: C, 73.7; H, 10.3%. A solution of 0.5 g of this compound in 20cc of benzene was treated with 20 g of p-toluene sulfonic acid and heated under reflux for 4 hr. The product 3$\beta$,25-diacetoxy-$\Delta^5$-cholestene (XIII) was isolated from ether and dissolved in 10cc of methanol and was treated with 1 cc of a 10% solution of potassium hydroxide. The reaction mixture was refluxed from 2 hr and the resulting 25-hydroxy cholesterol (IX) was isolated from ether. It had a m.p. of 180°–13 and was identified by comparison with an authentic sample.

The reactions of the process of the present invention are illustrated with reference to the following: Starting compounds (I) and (II) result in compounds (III) and (IV), respectively:

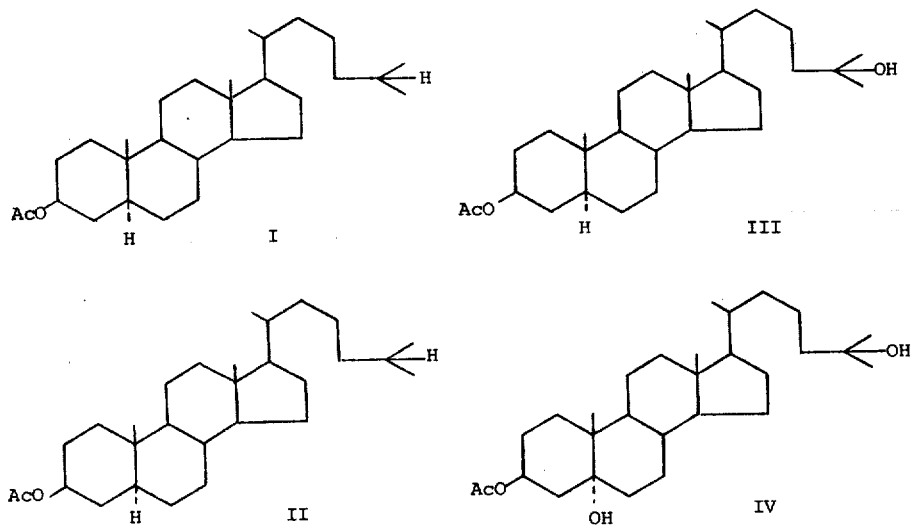

The compound (IV), above, was hydrolyzed to compound (VI), which latter was oxidized to yield compound (VII):

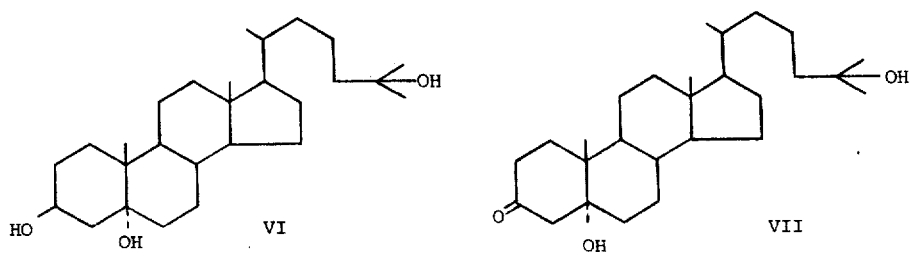

Compound (VII) was dehydrated to compound (VIII), which was converted to 25-hydroxy-7-dehydrocholesterol (V), by conventional means:

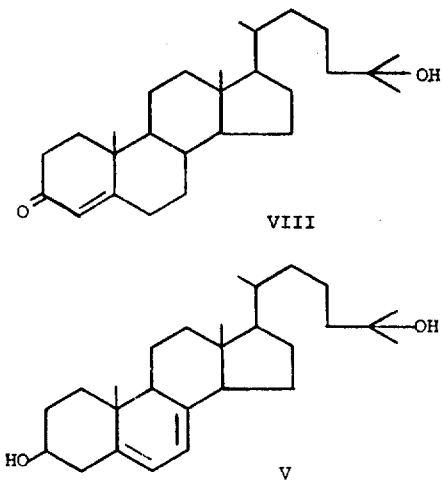

According to the other embodiment of the present invention, compound (IV) is converted to compound (IX), which is afterwards esterified to compound (X) or to compound (XI). The two latter esters can be dehydrated to yield compounds (XII) and (XIII), respectively. Hydrolysis of either of these, results in 25-hydroxycholesterol (IX). The latter was also obtained from $\Delta^4$-3-ketocholestane (VIII) after reduction of its enol-acetate:

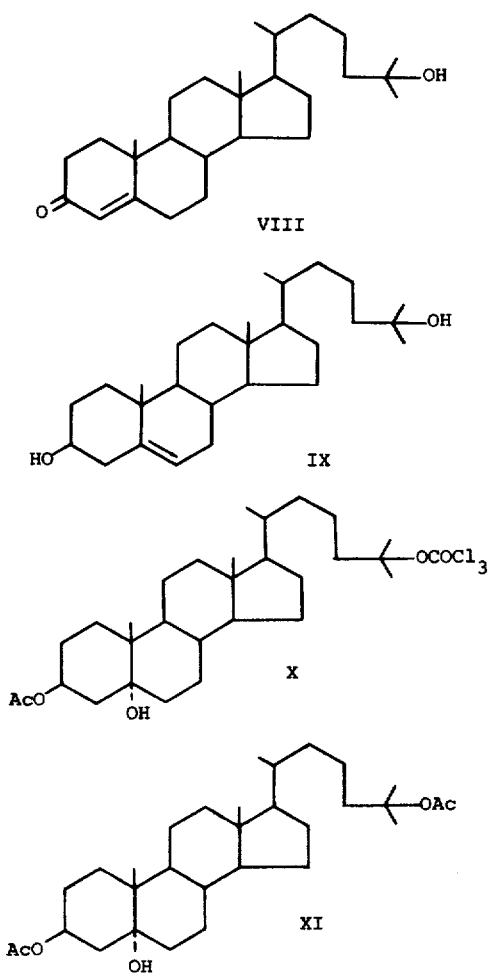

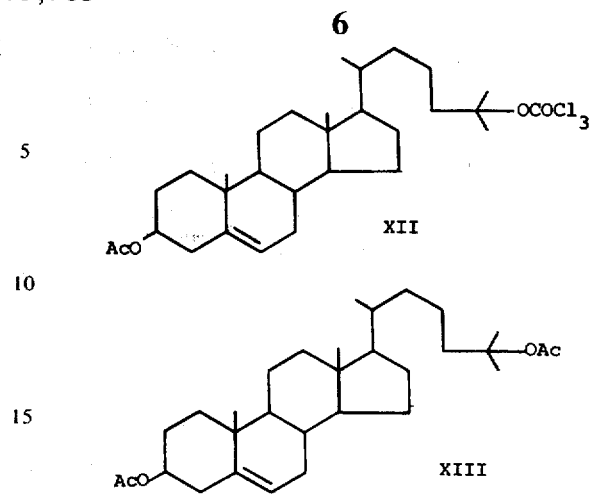

We claim:
1. A process for preparing derivatives of cholestane of the formula

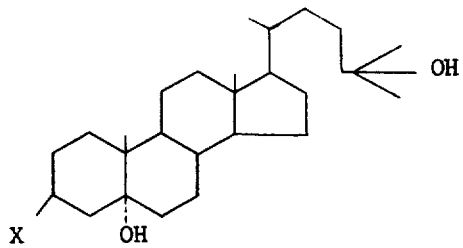

wherein X is —OH or —OCOCH$_3$, said process comprising subjecting 3β-acetoxy-5α-hydroxy cholestane, dissolved in a solvent, in the presence of peracetic acid to irradiation with ultra-violet light having a wavelength of less than 350 mμ, to form 3β-acetoxy-5α, 25-dihydroxy cholestane, removing the solvent, separating said 3β-acetoxy-5α,25-dihydroxy cholestane and converting same to the corresponding trihydroxy-derivative by treatment with an aqueous solution of an alkali metal hydroxide in a lower alkanol and dioxane.

2. A process as claimed in claim 1, wherein the starting material is 3β-acetoxy,5α-cholestane and one of the products is the corresponding 25-hydroxy derivative.

3. A process as claimed in claim 2, wherein a further product is 3β-acetoxy, 5α-hydroxy cholestane.

4. A process as claimed in claim 1, wherein the starting compound is 3β-acetoxy, 5α-hydroxy cholestane and the product comprises 3β-acetoxy, 5α-25-hydroxy cholestane.

5. A process as claimed in claim 4, wherein the obtained 3β-acetoxy, 5α, 25-dihydroxy cholestane is converted to 3β, 5α, 25-trihydroxy cholestane.

6. A derivative of cholestane having the formula wherein R is —OH, —OCOCCl$_3$ or —OCOCH$_3$.

7. A compound according to claim 6, wherein R is —OH.

8. A compound according to claim 6, wherein R is —OCOCCl$_3$.
9. A compound according to claim 6, wherein R is OCOCH$_3$.
10. A derivative of cholestane having the formula
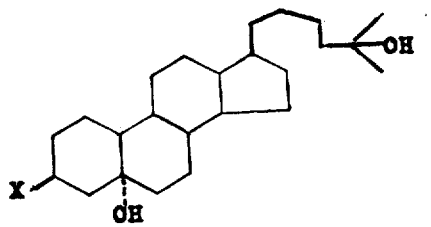
wherein X is =O or —OH.
11. A compound according to claim 10, wherein X is =O.
12. A compound according to claim 10, wherein X is —OH.
* * * * *